United States Patent
Yurko

(10) Patent No.: US 6,532,960 B1
(45) Date of Patent: Mar. 18, 2003

(54) AUTOMATIC RISE TIME ADJUSTMENT FOR BI-LEVEL PRESSURE SUPPORT SYSTEM

(75) Inventor: Gregory Yurko, Murrysville, PA (US)

(73) Assignee: Respironics, Inc., Murrysville, PA (US)

(*) Notice: Subject to any disclaimer, the term of this patent is extended or adjusted under 35 U.S.C. 154(b) by 0 days.

(21) Appl. No.: 09/896,644

(22) Filed: Jun. 29, 2001

Related U.S. Application Data

(60) Provisional application No. 60/216,999, filed on Jul. 10, 2000.

(51) Int. Cl.[7] ............ A61M 16/00; A62B 7/04; F16K 31/26
(52) U.S. Cl. ............ 128/204.26; 128/204.23
(58) Field of Search .......... 128/204.23, 204.21, 128/204.26, 204.22, 204.18, 205.23

(56) References Cited

U.S. PATENT DOCUMENTS

| | | |
|---|---|---|
| 5,148,802 A | 9/1992 | Sanders et al. |
| 5,239,995 A | 8/1993 | Estes et al. |
| 5,313,937 A | 5/1994 | Zdrojkowski |
| 5,433,193 A | 7/1995 | Sanders et al. |
| 5,513,631 A * | 5/1996 | McWilliams ............ 128/204.23 |
| 5,598,838 A * | 2/1997 | Servidio et al. ........ 128/204.21 |
| 5,794,614 A * | 8/1998 | Gruenke et al. ........ 128/202.22 |
| 5,865,173 A | 2/1999 | Froehlich |
| 5,931,160 A * | 8/1999 | Gilmore et al. ......... 128/204.18 |
| 2002/0023644 A1 * | 2/2002 | Berthon-Jones ......... 128/204.22 |

OTHER PUBLICATIONS

Tranquility Bilevel, A Comfortable Therapeutic Option, Jun. 18, 1999, Sales Brochure.
Branson, et al., Altering Flowrate during Maximum Pressure Support Ventilation (PSV max): Effects on Cardiorespiratory Function, Nov. 1990, pp. 1056–1064, vol. 35, No. 11.
MacIntyre, et al., Effects of Initial Flow Rate and Breath Termination Criteria on Pressure Support Ventilation, Jan. 1991, pp. 134–138.

* cited by examiner

Primary Examiner—William C. Doerrler
(74) Attorney, Agent, or Firm—Michael W. Haas

(57) ABSTRACT

An apparatus and method for a bi-level positive airway pressure support in which the rise time from the expiratory positive airway pressure to the inspiratory positive airway pressure is automatically controlled by the pressure support system. The pressure support system includes a sensor, a control system, and a pressure generating system. The sensor monitors the patient's respiration to detect respiratory events, such as an apnea, hyponea or other disturbance, and the control system responds to the sensor information to adjust the rise time from the expiratory positive airway pressure to the inspiratory positive airway pressure gas pressure to maximize patient comfort and pressure support treatment effectiveness.

18 Claims, 3 Drawing Sheets

AUTOMATIC RISE TIME ADJUSTMENT FOR BI-LEVEL PRESSURE SUPPORT SYSTEM

CROSS REFERENCE TO RELATED APPLICATIONS

The present invention claims priority under 35 U.S.C. §119(e) from U.S. provisional patent application No. 60/216,999 filed Jul. 10, 2000.

BACKGROUND OF THE INVENTION

1. Field of the Invention

The present invention generally relates to a bi-level positive airway pressure support system, and, more particularly, to a bi-level pressure support system and method of providing bi-level pressure support in which the rise time from the expiratory phase of pressure support to the inspiratory phase is automatically adjusted.

2. Description of the Related Art

Pressure support systems that provide a flow of breathing to an airway of a patient at an elevated pressure to treat a medical disorder are well known. One basic form of pressure support system is a continuous positive airway pressure (CPAP) system, which typically involves providing a flow of breathing gas, such as air, to a patient's airway at a constant pressure throughout a patient's breathing cycle. When used to treat obstructive sleep apnea (OSA), for example, this constant pressure is provided at a level sufficient to overcome a patient's airway resistances.

It is also known to provide a bi-level positive pressure therapy in which the pressure of gas delivered to the patient varies with the patient's breathing cycle. In a bi-level pressure support system, an inspiratory positive airway pressure (IPAP) is provided during a patient's inspiratory phase of the breathing cycle and an expiratory positive airway pressure (EPAP) is provided during the expiratory phase. The EPAP is lower than the IPAP so that the patient exhales against relatively low pressure as compared to the IPAP pressure, thereby increasing the comfort to the patient. The BiPAP® family of pressure support devices manufactured by Respironics, Inc. of Murrysville, Pa., are examples of pressure support device that provide this bi-level form of pressure support therapy. In addition, several U.S. patents describe this bi-level pressure support system in detail, including U.S. Pat. Nos. 5,433,193; 5,313,937; 5,239,995; and 5,148,802, all of which are hereby expressly incorporated herein by reference as if set forth in their entirety herein.

With the improved effectiveness of bi-level pressure support systems over their progeny, CPAP systems, the emphasis has shifted to creating bi-level pressure support systems that are more comfortable for a patient to use without sacrificing treatment effectiveness. It is anticipated that a more comfortable pressure support system will be more frequently and more correctly used by the patient.

U.S. Pat. No. 5,927,274 discloses a bi-level pressure support system that transitions from EPAP and IPAP over a rise time interval, which typically has a length of several hundreds of milliseconds. The '274 patent provides the operator with the ability to manually adjust this rise time interval to increase patient comfort. While the manual rise time selection technique taught by the '274 patent is a step toward increasing patient comfort, it is also burdensome, because the operator must manually adjust the rise time setting as needed via a control input on the pressure support device. This can require numerous adjustments over relatively short periods of time if patient comfort is to be optimized. It can be appreciated that there is perceived a need for a pressure support system with increased patient comfort with little or no resultant decrease in therapy effectiveness and that minimizes the amount of operator intervention required to implement the improved pressure support therapy effectively.

SUMMARY OF THE INVENTION

Accordingly, it is an object of the present invention to provide a bi-level pressure support system that overcomes the shortcomings of conventional pressure support systems. This object is achieved according to one embodiment of the present invention by providing a bi-level pressure support system that includes a pressure generating system that produces a flow of breathing gas at an inspiratory positive airway pressure and an expiratory positive airway pressure. A conduit delivers the flow of breathing gas to an airway of a patient. A sensor detects a physiological condition of the patient, such as whether the patient is experiencing a breathing disorder. A control system controls the output of the pressure generating system to automatically adjust the rise time from the inspiratory positive airway pressure to the expiratory positive airway pressure based on the output of the sensor. Preferably, the control system increases the rise time in the absence of breathing disorders to increase patient comfort.

It is yet another object of the present invention to provide a method of providing bi-level pressure support that does not suffer from the disadvantages associated with conventional pressure support techniques. This object is achieved by providing a method that includes producing a flow of breathing gas at an inspiratory positive airway pressure and an expiratory positive airway pressure that is less than the inspiratory positive airway pressure, detecting a physiological condition of a patient receiving the flow of breathing gas, and determining a rise time from the inspiratory positive airway pressure to the expiratory positive airway pressure based on the physiological condition of the patient. The rate of change from the inspiratory positive airway pressure to the expiratory positive airway pressure is controlled based on this rise time.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

As discussed above, a bi-level pressure support system provides an inspiratory positive airway pressure (IPAP) during inhalation and an expiratory positive airway pressure (EPAP) during exhalation to the airway of a patient. For most patients requiring bi-level therapy, a higher IPAP pressure is required to maintain airway patency during inhalation, and a much lower EPAP pressure is sufficient to maintain airway patency during exhalation. In fact, it is known to set the EPAP level as low as atmospheric pressure for some patients. By providing bi-level pressure support with the lowest necessary EPAP pressure, the work required for the patient to exhale is reduced and, therefore, the patient's comfort is increased. This, in turn, promotes patient compliance with the prescribed therapy.

Figure 1A:
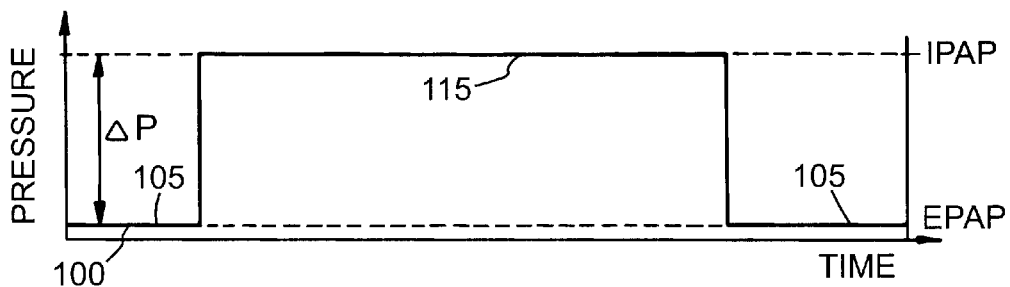
FIG. 1A shows a theoretical pressure curve.

FIG. 1A schematically depicts a theoretical pressure curve 100 output by a bi-level positive airway pressure support system over a portion of a patient's breathing cycle. During an expiratory phase of the breathing cycle, pressure curve 100 is at the expiratory pressure 105. At the end of exhalation, i.e., at the onset of the subsequent inhalation, pressure curve 100 changes to an inspiratory pressure 115. When the system detects the end of inspiration, i.e., at the onset of the subsequent exhalation, pressure curve 100 returns to the lower expiratory pressure 105, and the cycle starts over. The difference in pressure between EPAP 105 and IPAP 115 is designated as $\Delta P$ in FIG. 1. This pressure change occurs instantaneously in the FIG. 1A theoretical model. Thus, FIG. 1A shows pressure curve 100 as a square wave.

Figure 1B:
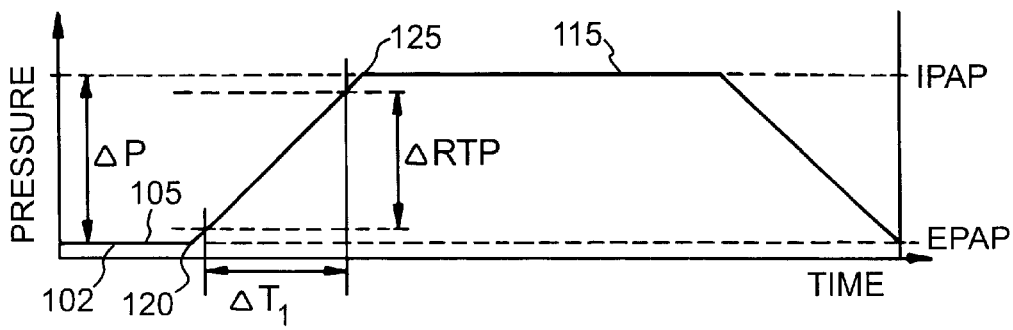
FIGS. 1B, 1C, and 1D show a pressure curve having an average rise time (FIG. 1B), a pressure curve having a shorter rise time (FIG. 1C), and a pressure curve having a longer rise time (FIG. 1D) that are capable of being generated by the pressure support system of the present invention.

Patient comfort may not be optimized if the ideal pressure curve is applied to the patient. More specifically, rather than an instantaneous transition from EPAP to IPAP, patient comfort may be optimized if a slightly more gradual transition is made from EPAP to IPAP and vise versa. FIG. 1B shows such a ramping of a pressure curve 102 from EPAP 105 to IPAP 115. This ramping effect is measured by the time it takes the system pressure to increase from EPAP 105 to IPAP 115 and is referred to as the "rise time" of the bi-level pressure support system. Similarly, rather than an instantaneous transition from IPAP to EPAP, FIG. 1B shows ramping of the system pressure from IPAP 115 to EPAP 105. This ramping effect is measured by the time it takes the system pressure to decrease from EPAP 105 to IPAP 115 and is referred to as the "fall time" of the bi-level pressure support system.

Accordingly, the rise time of a bi-level pressure support system is generally a measure of the time for the system pressure to change from the expiratory pressure to the inspiratory pressure, and fall time is a measure of the time for the system pressure to change from the inspiratory pressure to the expiratory pressure. However, rather than measure rise time from the peak-to-peak between EPAP and IPAP, the rise time can also be defined as the time it takes for the system pressure to change from a percentage, such as 10%, of its initial pressure value to a percentage, such as 90%, of its final pressure value. With respect to a system pressure change ($\Delta P = IPAP - EPAP$) from a lower EPAP to a higher IPAP value, the 10% initial pressure is defined as:

$$EPAP + 0.10 \times (IPAP - EPAP),$$

and the final 90% pressure is defined as:

$$EPAP + 0.90 \times (IPAP - EPAP).$$

Figure 1C:
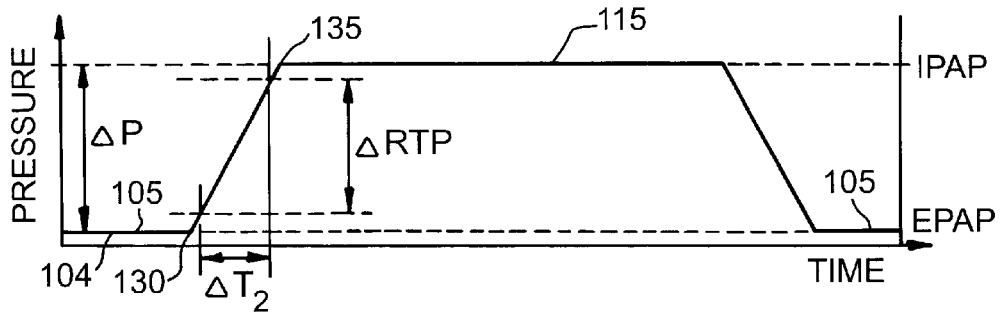
Figure 1D:
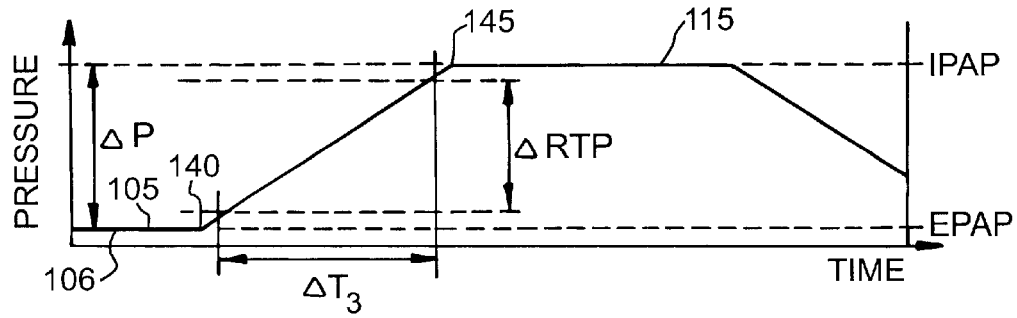

This 10% to 90% pressure change is shown in FIGS. 1B, 1C, and 1D as $\Delta RTP$.

Likewise, the fall time can also be defined as the time it takes for the system pressure to go from 90% of its initial pressure to 10% of its final pressure when a fall from the higher IPAP value to the lower EPAP value is calculated. Thus, one may calculate separate rise and fall times for each specific transition (low-to-high or high-to-low). Rise time is generally between 0.1 to 0.3 seconds for the pressure support system of the present invention.

FIGS. 1B–1D each show the pressure differential from 10%–90% of final IPAP value as $\Delta RTP$ and the corresponding rise time as $\Delta T$. As shown in FIG. 1B, the cycle begins with the system pressure 102 at EPAP level 105. When the pressure support system detects that the patient has finished expiration or has begun inspiration, or that some other prompting event has occurred, the system pressure is ramped up toward IPAP level. The start of the rise time pressure ramp is indicated at 120 in FIG. 1B. The ramping is shown as a straight line in FIG. 1B, but the ramping may also be an exponential ramp or any other transitional waveform from one generally constant level to another. However, it is to be understood that the IPAP and/or EPAP pressure need not necessarily be constant. See, for example, U.S. Pat. Nos. 5,535,738 and 5,794,615, as well as U.S. patent application Ser. No. 09/041,195, which teach varying the IPAP and/or EPEP pressure as a function of patient flow or a preestablished flow profile, the contents of each of which are incorporated herein by reference. Ultimately, the system pressure reaches its intended IPAP value at a point in pressure curve 102 indicated at 125 and levels off at to IPAP 115. This smooth ramping is characterized by a rise time $\Delta T_1$ and a pressure change $\Delta RTP$.

It is generally believed that shorter rise times ($\Delta T$) result in a decrease in comfort to the patient because of the "sharper" transient in pressure. However, shorter rise times are also believed to result in an increase in system therapeutic effectiveness. FIG. 1C illustrates rise time $\Delta T_2$ that begins at point 130 in pressure curve 104 and ends at point 135, so that rise time $\Delta T_2$ is shorter than rise time $\Delta T_1$, which will likely result in decreased patient comfort but increased therapy effectiveness.

FIG. 1D illustrates rise time $\Delta T_3$ that begins at point 140 in pressure curve 106 and ends at point 145, so that rise time $\Delta T_3$ is longer than rise time $\Delta T_1$, which will likely result in increased patient comfort, but decreased therapy effectiveness. It can thus be appreciated that there is a tradeoff between patient comfort (longer rise time) and effective treatment (shorter rise time). As will be appreciated below, the present invention, in accordance with at least one presently preferred embodiment, seeks to maximize patient comfort while maintaining sufficiently effective respiratory treatment by automatically selecting an optimal rise time to suit the needs of the patient. The present invention also contemplates automatically adjusting the fall time, such as to correspond to a mirror image of the pressure curve during the rise time interval. Of course, the fall time can remain unchanged despite variations in the rise time.

Generally, in at least one embodiment of the present invention, the rise time of a ventilator or other pressure support system is automatically adjusted based on physiological conditions of the patient detected by flow, pressure, and other sensors. The rise time may preferably begin with a maximal value, thus lending maximal user comfort, and decreased as necessary, such as in accordance with the detection of apenic events, such as an apnea, hyponea, upper airway resistance, or snoring. The event detection can employ existing techniques, for example, based on flow limitations, upper airway noise, or both. If an apenic event is detected, the rise time can be shortened or decremented. During the continued detection of apenic events or other detected problems, the rise time may be shortened once per minute (or other time interval according to a preset level) until it has been lowered to a minimum rise time. When five minutes (or some other preset amount of time) elapses with no detection of an apenic event, the rise time is lengthened by a preset incremental amount. During the continued absence of apenic events, this rise time lengthening continues until the rise time reaches a maximum allowed rise time. Preferably, the rise time minimum and incremental increase and decrease amounts are determined empirically via clinical evaluation, but the maximum rise time is preferably calculated dynamically based on the inspiratory time of breathing.

The present invention contemplates that a rise time adjustment algorithm is processed continuously by the pressure support system during operation, resulting in continuous adjustment to the rise time to maximize patient comfort while minimizing operator intervention. The rise time will vary as the algorithm determines the maximum possible rise time for patient comfort while maintaining sufficient therapy. Because the rise time is automatically adjusted, the rise time necessary for sufficient therapy may be optimized from patient to patient, from night to night, and even from minute to minute on a particular patient and does not require any intervention of the patient or caregiver.

The present invention contemplates that the algorithm is implemented in a microprocessor-based bi-level pressure support system. Such a system preferably has one or more sensors to produce a pressure signal, flow signal, pressure and flow signals, or some other sensor signal, available to the microprocessor for triggering and cycling. The pressure support system also preferably includes control hardware to allow the microprocessor to vary the rise time as determined by the implementation of the algorithm. For example, suitable pressure support devices that can be used to implement the automatic rise time control of the present invention are the BiPAP® Duet® Bi-level System or BiPAP® Duet®LX Bi-level System, both of which are manufactured by Respironics, Inc., of Murrysville, Pa. Such pressure support devices have a microprocessor, memory, pressure and flow sensors, and can be programmed in C or some other computer language.

Figure 2:
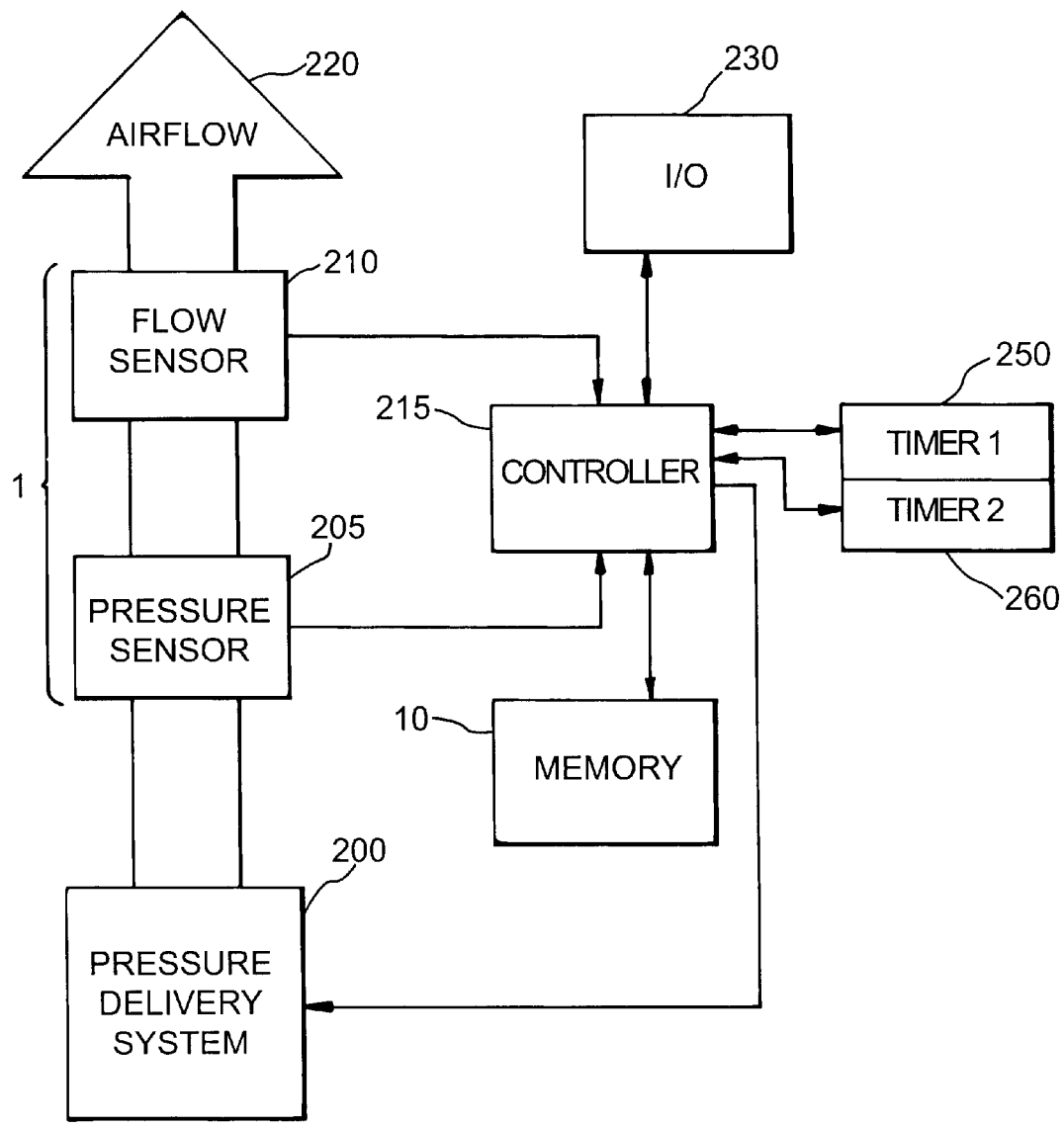
FIG. 2 is a schematic block diagram of a positive airway pressure support system with automatically adjustable rise time according to one preferred embodiment of the present invention.

FIG. 2 shows a general block diagram of a bi-level pressure system support system 190 with automatic rise time adjustment according to one preferred embodiment of the present invention. Bi-level pressure support system 190, as shown, includes a pressure generating system 200, sensors 204, represented by a pressure 205 and a flow 210 sensor, and a controller 215 for controlling the operation of the ventilator and for carrying out the automatic rise time adjustment. Bi-level pressure support system 190 also includes an input/output device 230, for example, for inputting operating variables into the system and for reviewing its operation. A memory 240 stores such variables, as well as information gathered or determined by controller 215, such as the occurrence of apenic events. Bi-level pressure support system 190 further includes a first timer 250 and a second timer 260, the operation of which are discussed in detail below.

In FIG. 2, the flow of pressurized air or other gas imparted to the user or patient is represented by an airflow arrow 220. In actual practice, this airflow 220 may be communicated to the user's respiratory system by way of a patient circuit, such as flexible plastic tubing, attached to a patient interface device, such as a nasal mask, nasal/oral mask, full face mask, total face mask, hood, nasal cannula, tracheal tube, or endotracheal tube, for communicating a flow of gas in the patient circuit with an airway of the user.

Pressure generating system 200 generates a flow of breathing gas that is provided to the user. In a preferred embodiment of the present invention, pressure generating system 200 includes a means for generating a flow of breathing gas, such as blower, impeller, or fan rotated by a motor, a piston, or bellows to generate a flow of breathing gas. Because the pressure in a bi-level pressure support system changes depending on whether the system is generating an expiratory or an inspiratory positive airway pressure, the pressure generating system preferably includes a means for controlling the pressure of the flow of breathing gas communicated to the patient circuit, and, hence, to the airway of the patient. Typically, a constant pressure blower, i.e., a blower driven by a motor to output a constant pressure, is used to generate a flow of breathing gas, and a pressure/flow control valve, which is typically although not necessarily, downstream of the constant pressure blower, controls the pressure of the flow of breathing gas provided to the patient circuit, and, hence, provided to the airway of the patient. The blower itself can also provide different air pressures, for example by varying the operating speed of the blower. Blower speed and a pressure control valve can be used independently or in unison to control the pressure of the flow of breathing gas delivered to the airway of the patient.

Sensors 204, such as flow sensor 210 and pressure sensor 205, preferably monitor the conditions of the user's respiratory system to detect when an apenic event occurs by monitoring the flow and pressure of breathing gas in the patient circuit. These sensors can be of numerous types, but flow and pressure sensors are common examples sensors well know for accomplishing this functions. The output of these sensors is typically used to trigger and cycle the pressure support system or to perform a function when an apenic event or other disturbance is detected, such as increase the IPAP pressure. It is to be understood that the present invention contemplates using other patient monitoring devices as sensors 204, and such sensors need not be necessary associated with the pressure generating system or patient circuit. For example, it is known to use a plethysmography belt, EMG sensors, motion detectors, temperature sensors and other devices to detect patient respiration. It is also know to detect respiration based on the energy provided to the motor in the pressure support system. Thus, sensors 204 encompass any means for detecting a physiological condition of the patient.

Generally, the above sensors, pressure/flow generating and delivery arrangement, and control circuit work together as a positive airway pressure support system. The sensors preferably detect various conditions of the system and the patient's breathing pattern to provide information to the control system. The control system, which is preferably microprocessor-based, uses this acquired information to monitor the patient's breathing, for example, to determine whether any apenic events or other conditions occur, and/or to control how the rise time and other aspects of the pressure delivered to the patient should be altered, updated, or controlled. For instance, the control system may determine a new rise time based on the detection of an apenic event.

This new rise time is communicated to the pressure delivery system to either change the blower pressure directly or change the pressure valve setting to impart a different air or gas pressure to the patient.

Figure 3:
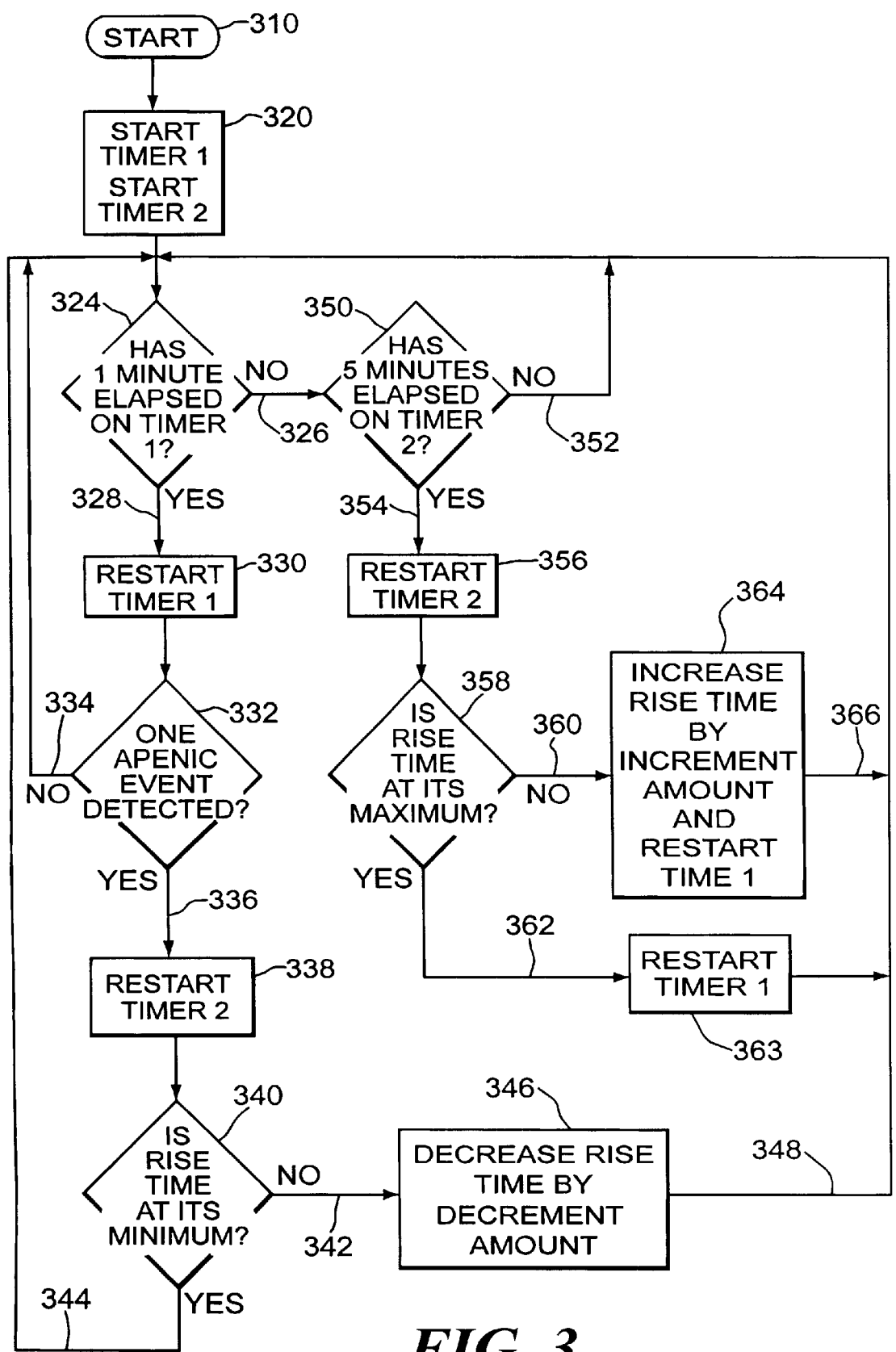
FIG. 3 is a flow chart of the control system used in one preferred embodiment of the pressure support system of the present invention.

FIG. 3 shows an exemplary algorithm that controller 215 uses to adjust the rise time of the bi-level pressure support system in accordance with one presently preferred embodiment of the invention. This algorithm is represented by a flow chart where the square chart entries represent a system function and the diamond-shaped entries represent a decision that the control circuit makes.

The control system that operates according to the algorithm of FIG. 3 may use several different variable values and system settings. First, there is an actual, or computed, system rise time. This value may be communicated to the pressure delivery system and represents the rise time $\Delta T$ from FIGS. 1B–1D. This rise time exists between the range of two variables: the maximum rise time and the minimum rise time. The minimum rise time is preset by either the patient's doctor or a knowledgeable patient or other person and represents the shortest rise time that the bi-level pressure support system will allow. This limit is placed on the system for patient safety or comfort. On the other hand, the maximum rise time may either be preset, like the minimum rise time, or may be determined by the control system. Up to a point, the higher this maximum rise time, the greater the comfort the patient should enjoy while using the bi-level pressure support system. This maximum rise time value may also be limited.

Also, the bi-level pressure support system may have either a preset or dynamically controlled value for incrementing and/or decrementing the system rise time. When the controller determines that the rise time of the system pressure must be updated, the increment and decrement values represent a length of time by which the calculated rise time is lengthened or shortened. These values may be set individually because, for example, the rise time decrement amount, which aids in therapy, may be higher than the rise time increment amount, which is based on patient comfort.

There may also be two rise time adjustment control variables based on a doctor or patient defined setting. The first variable, called for example, "ApenicCheck," determines the time period over which the system will check for apenic events and how many apenic events within that time frame are sufficient to cause the system to alter the rise time. The time component of the ApenicCheck variable is preferably compared to a running timer during system operation to determine when the window over which the control circuit examines the sensor data for apenic events opens and closes. This value may be preset and constant during system operation, or the value may be dynamically changed, for example, during and soon after apenic events are sensed. The exemplary value of this variable in FIG. 3 is one minute. The number of apenic events component of the ApenicCheck variable, which indicates how many apenic events can occur within that time frame before the system will increment the rise time, may also be preset and constant during system operation, or the value may be dynamically changed, for example, during and soon after apenic events are sensed. As described in greater detail below, in FIG. 3, the presence of one apenic event within the one minute window may be sufficient to cause an increase in the rise time.

The second variable, called, for example, "RiseTimeWait," determines how long the system will wait before lengthening the system rise time, and, therefore, make the patient more comfortable. This value will often be above zero to allow the patient's respiratory system sufficient time to get used to the current rise time setting before a new rise time is calculated. Again, this variable may be preset or dynamically changed. The example value of this variable in the algorithm of FIG. 3 is five minutes.

The bi-level pressure support system of the present invention operates in accordance with the algorithm of FIG. 3 to control the rise time by starting at step 310. In the step 320, each of two timers, Timer 1 and Timer 2, are set to an initial value of zero. These timers both begin counting the elapsed seconds up from zero after they are reset. The first timer, Timer 1, is compared to the time component of the ApenicCheck variable to determine the window over which the system needs to check for a recent apenic event. The second counter, Timer 2, is compared to the RiseTimeWait variable to determine if the specified amount of time has elapsed since the last apenic event or the last rise time lengthening.

After resetting and starting the timers in step 320, the algorithm, in step 324, compares the first timer to the stored value of the time component of the ApenicCheck variable to determine the time period during which the system monitors for apenic events. In FIG. 3, this stored value is shown as one minute, but this value can be set to any desired level. The time component of the ApenicCheck variable should be set to a value that allows the system to adjust the rise time to response relatively rapidly to changes in the patient's condition, while not overreacting to such changes. The time component of the ApenicCheck variable should not be made too long or the system will not effectively response to the apenic events. On the other hand, time component of the ApenicCheck variable should not be made too short or the system may change the rise time too frequently, which may in turn wake or disturb the patient.

If less than one minute has elapsed since the first timer has been reset, the algorithm follows path 326 to decision block 350. If, on the other hand, one minute or more has elapsed on the first timer since the timer has been reset, the algorithm follows path 328 to function block 330.

In step 330, the first timer, Timer 1, is reset so that another one minute interval can be counted off during which the system again checks for an apenic event. The algorithm proceeds to step 332 where the input from the flow, pressure, or other sensors is analyzed to determine if one or more apenic events have been detected during the one minute interval. As described above, these sensors will preferably trigger a response from the control system when certain conditions, such as apenic events, are detected. The number of such events in the set time frame are stored and compared to a threshold value in step 332. In the illustrated embodiment, if one apenic event occurs, the system proceeds to step 338. It is to be understood that the threshold number of apenic events can be a value other than one, and this threshold number of events can be adjusted manually or dynamically during the operation of the system.

In FIG. 3, if no apenic event, or if the number of apenic events is less than the threshold requirement set in step 332 occur in the time frame set in step 324, the program follows path 334 back to block 324. In this case, no apenic events have occurred, the patient is resting quietly, and the rise time does not need to be decreased to increase the flow of air to the patient. This is the normal flow of the rise time control method or program.

If a check of the pressure, flow, or other sensors in block 332 shows that an apenic event has occurred, path 336 is followed to function block 338 where the second timer, Timer 2, is reset to zero seconds. Timer 2 keeps track of the time since either an apenic event or a rise time increment has occurred. In step 338, Timer 2 is reset due to the occurrence of the apenic event. After resetting the second timer, the system responds to the detected event by attempting to shorten the system pressure rise time (thereby increasing therapeutic effect). In FIG. 3, the algorithm proceeds to decision block 340, where the actual rise time is compared to its minimum allowed value set by the doctor or the patient. If the rise time is at its minimum, then the rise time should remain at this minimum value despite the detection of a recent apenic event. Thus, path 344 is followed to return to decision block 324. Although theoretically, the rise time should be shortened to increase therapeutic effect, the automatic rise time adjustment program will not decrease the rise time below the minimum safety values set by the patient's doctor or by knowledgeable patients themselves.

If the rise time is not at its minimum allowed value, then the recent apenic event detected in block 332 causes the algorithm to proceed along path 342 to function block 346. At block 346, the rise time is decreased by the preset decrement amount. As stated before, this amount can be selected by the user or the patient's doctor while initializing the machine, or the value can be dynamically set by the system. The rise time is decreased because the pressure and flow sensors detected an apenic event indicating that the patient is having trouble breathing at the current rise time level. Hence, the shorter rise time will cause the bi-level pressure support system to change from one pressure level to another in a shorter amount of time. Although less comfortable for the patient, this decremental change may eliminate a more severe breathing episode for the patient. This automatic adjustment may correct the apenic abnormality without waking or disturbing the patient. This makes the overall system more responsive and comfortable.

After either adjusting the rise time value via path 348 or not adjusting the rise time via path 344, the algorithm will return to decision block 324. Here, Timer 1 is again compared to the time component of the ApenicCheck variable. If Timer 1 is less than one minute, then decision block 324 will return a negative value, and the algorithm will proceed along path 326 to the Timer 2 decision block 350. In block 350, the elapsed time of the second timer is compared to the RiseTimeWait value, which is shown as being five minutes in block 350. This block 350 will return a negative value if an apenic event or rise time increment has occurred within the last five minutes. If so, the algorithm will proceed along path 352 back to the first timer decision block 324. If the second timer decision block 350 returns a negative value, then program path 354 is followed to function block 356 where Timer 2 is reset to zero seconds. This timer is reset because an apenic event has not occurred within five minutes and the rise time has not been shortened within five minutes.

At this stage, the control circuit has effectively determined that the patient's breathing has been normal for at least five minutes, and the program seeks to increase patient comfort by increasing rise time. The algorithm proceeds to block 358 where the system rise time is compared to the maximum rise time entered by the patient or her doctor. If the rise time is at its maximum, then the patient is as comfortable as the preset limits allow, and the automatic rise time adjuster will not increase the rise time beyond this preset value. Even though a longer rise time theoretically may result in the patient being more comfortable, the preset limits should not be traversed in the interest of patient safety. Hence, path 362 will be taken to step 363 where Timer 1 is also reset to reestablish the window over which the system will check for apenic events and then the system will return back to the first timer comparison block 324, and the circuit will start over.

If the decision block 358 determines that the rise time is not at its preset maximum value, then the algorithm proceeds along path 360 to function block 364. Here, the system rise time is incremented by the preset amount to make the user more comfortable. In addition, Timer 1 is reset to reestablish the window over which the system will check for apenic events. The algorithm then follows path 366 and the cycle starts over in block 324 where Timer 1 is again compared to the time component of the ApenicCheck variable.

The above algorithm has been provided for illustrative purposes only and should not be construed to limit the present invention to any particular combination of algorithm steps, variables, or algorithm procession. The above circuit may contain elements or steps that can be replaced by other steps or steps that may be ignored altogether. There are also many additional steps, variables, and elements that may be used in addition to the above system, and that are fully encompassed by the disclosure herein. For example, rather than look for x number of apenic events in a y time period, as discussed above with respect to steps 324 and 332, the system could look for the frequency at which such events are occurring. If they apenic events are occurring less than one minute apart, for example, the rise time can be shortened.

It should be noted that the above control algorithm for the respirator control arrangement could be easily implemented on a microprocessor-based system. In such a system, the microprocessor may include a memory to store preset maximum and minimum system pressures, pressure increment/decrement values, or other values which are calculated during ventilator operation. The microprocessor-based system may also include an arithmetic logic unit for calculating the updated pressure rise time based on the values inputted to the microprocessor or stored in the memory. The function and structure of this microprocessor-based control arrangement may be complex, with additional features and components, and all such embodiments are contemplated within the scope of this invention and disclosure.

Alternatively, the automatic rise time system could be hard-wired or may exist as part of a non-microprocessor-based system. Simple electronic components such as resistors, capacitors and inductors can be combined in presently known ways to create timing circuits, and circuits that respond to input information. The above example was illustrated only by way of example to show one possible embodiment of the present invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered by way of example only to facilitate comprehension of the invention and should not be construed to limit the scope thereof.

What is claimed is:

1. A pressure support system comprising:

a pressure generating system adapted to produce a flow of breathing gas at an inspiratory positive airway pressure (IPAP) level and an expiratory positive airway pressure (EPAP) level that is less than the IPAP level;

a conduit operatively coupled to the pressure generating system to deliver the flow of breathing gas to an airway of a patient;

a sensor adapted to detect a physiological condition associated with such a patient receiving the flow of breathing gas; and a processor receiving an output of the sensor and providing a control signal to the pressure generating system, wherein the processor is programmed to control the pressure generating system so as to:

a) deliver the flow of breathing gas to such a patient at the IPAP level during at least a portion of an inspiratory phase of such a patient, and to deliver the flow of breathing gas to such a patient at the EPAP level during at least a portion of an expiratory phase of such a patient, b) maintain the IPAP level and the EPAP level at a substantially fixed value over a plurality of respiratory cycles of the patient, and c) automatically adjust a rise time from the EPAP level to the IPAP level during the plurality of respiratory cycles based on the output of the sensor.

2. The pressure support system of claim 1, further comprising:

an input/output device operatively coupled to the processor; and at least one timer operatively connected to the processor, wherein the processor determines whether to adjust the rise time from the EPAP level to the IPAP level based on an output of the timer.

3. The pressure support system of claim 2, wherein the input/output device is used to set at least one of (1) a time interval during which the processor checks an output signal from the sensor to determine whether to adjust the rise time, (2) a number of apneic events that can occur in the time interval before the processor will adjust the rise time, and (3) an amount by which the rise time is incremented or decremented by the processor.

4. The pressure support system of claim 1, wherein the processor dynamically determines at least one of (1) a time interval during which the processor checks an output signal from the sensor to determine whether to adjust the rise time, (2) a number of apneic events that can occur in the time interval before the processor will adjust the rise time, and (3) an amount by which the rise time is incremented or decremented by the processor.

5. The pressure support system of claim 1, wherein the sensor is a flow sensor, a pressure sensor associated with the conduit, or both.

6. The pressure support system of claim 1, wherein the processor controls the pressure generating system so as to adjust a fall time from the IPAP level to the EPAP level.

7. A pressure support system comprising:

pressure generating means for producing a flow of breathing gas at an inspiratory positive airway pressure (IPAP) level and an expiratory positive airway pressure (EPAP) level that is less than the IPAP level;

sensing means for detecting a physiological condition associated with a patient receiving the flow of breathing gas; and controlling means, operatively connected to the sensing means and the pressure generating means, for:

a) determining a rise time from the EPAP level to the IPAP level based on an output of the sensing means, b) causing the pressure generating means to deliver the flow of breathing gas to such a patient at the IPAP level during at least a portion of an inspiratory phase of such a patient, and to deliver the flow of breathing gas to such a patient at the EPAP level during at least a portion of an expiratory phase of such a patient, c) maintaining the IPAP level and the EPAP level at a substantially fixed value over a plurality of respiratory cycles of the patient, and d) controlling a rate of change from the EPEP level to the IPAP level over the plurality of respiratory cycles based on the rise time.

8. The pressure support system of claim 7, wherein the controlling means includes a microprocessor.

9. The pressure support system of claim 7, wherein the controlling means includes a memory for storing a value of pressure support system variables.

10. The pressure support system of claim 7, further comprising:

inputting means, operatively coupled to the controlling means, for providing information thereto; and timing means, operatively connected to the controlling means, wherein the controlling means determines whether to adjust the rise time from the EPAP level to the IPAP level based on an output of the timing means.

11. The pressure support system of claim 7, wherein the sensing means comprises a flow sensor, a pressure sensor associated with the pressure generating means, or both.

12. The pressure support system of claim 7, wherein the controlling means dynamically determines at least one of (1) a time interval during which the controlling means checks an output signal from the sensing means to determine whether to adjust the rise time, (2) a number of apneic events that can occur in the time interval before the controlling means will adjust the rise time, and (3) an amount by which the rise time is incremented or decremented by the controlling means.

13. The pressure support system of claim 7, wherein the controlling means also controls the pressure generating means so as to adjust a fall time from the IPAP level to the EPAP level.

14. A method for automatically adjusting a rise time of a pressure support system, comprising:

producing a flow of breathing gas at an inspiratory positive airway pressure (IPAP) level and an expiratory positive airway pressure (EPAP) level that is less than the inspiratory positive airway pressure;

detecting a physiological condition associated with a patient receiving the flow of breathing gas;

determining a rise time from the EPAP level to the IPAP level based on the physiological condition associated with such a patient;

delivering the flow of breathing gas to such a patient at the IPAP level during at least a portion of an inspiratory phase of such a patient, and delivering the flow of breathing gas to such a patient at the EPAP level during at least a portion of an expiratory phase of such a patient;

maintaining the IPAP level and the EPAP level at a substantially fixed value over a plurality of respiratory cycles of the patient; and controlling a rate of change from the EPAP level to the IPAP level based on the rise time.

15. The method according to claim 14, further including setting at least one of (1) a minimum allowed rise time, (2) a maximum allowed rise time, (3) an amount for each incremental change in rise time, and (4) an amount for each decremental change.

16. The method according to claim 14, further including dynamically determining at least one of (1) a time interval during which the physiological condition is checked, (2) a number of apneic events that can occur in the time interval before the rise time is adjusted, and (3) an amount by which the rise time is incremented or decremented.

17. The method according to claim 14, wherein the rise time is decreased responsive to detecting an apneic event of a patient.

18. The method according to claim 14, wherein the rise time is increased after a period of time in which no apneic events are detected.

* * * * *